US006953796B2

(12) United States Patent
Bigot et al.

(10) Patent No.: US 6,953,796 B2
(45) Date of Patent: Oct. 11, 2005

(54) USE OF 2-AMINO-THIAZOLINE DERIVATIVES AS INHIBITORS OF INDUCIBLE NO-SYNTHASE

(75) Inventors: Antony Bigot, Massy (FR); Jean-Christophe Carry, Saint Maur Des Fosses (FR); Serge Mignani, Chatenay-Malabry (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 10/764,853

(22) Filed: Jan. 26, 2004

(65) Prior Publication Data

US 2004/0157843 A1 Aug. 12, 2004

Related U.S. Application Data

(63) Continuation of application No. 10/291,084, filed on Nov. 8, 2002, now Pat. No. 6,699,867.
(60) Provisional application No. 60/352,797, filed on Jan. 30, 2002.

(30) Foreign Application Priority Data

Nov. 9, 2001 (FR) .......................................... 01 14510

(51) Int. Cl.$^7$ .................... A61K 31/381; A61K 31/427; A61K 31/5377; C07D 417/06
(52) U.S. Cl. ............................. 514/236.8; 514/254.02; 544/133; 544/369
(58) Field of Search ........................ 514/236.8, 254.02; 544/369, 133

(56) References Cited

U.S. PATENT DOCUMENTS

| | | | | |
|---|---|---|---|---|
| 6,420,566 B2 | * | 7/2002 | Carry et al. | 548/184 |
| 6,451,821 B1 | * | 9/2002 | Carry et al. | 514/342 |
| 6,699,867 B2 | * | 3/2004 | Bigot et al. | 514/236.8 |
| 2003/0225140 A1 | * | 12/2003 | Bacque et al. | 514/342 |
| 2004/0192745 A1 | * | 9/2004 | Ehrenreich et al. | 514/367 |

FOREIGN PATENT DOCUMENTS

| WO | WO 94/12165 | 6/1994 |
|---|---|---|
| WO | WO 95/11231 | 4/1995 |
| WO | WO 96/14842 | 5/1996 |

OTHER PUBLICATIONS

Lala, P.K. and Orucevic, A., "Role of nitric oxide in tumor progression: Lessons from experimental tumors," Cancer and Metastasis Reviews (1998), 17(1):91–106.*
Cummings, Jeffrey L., "Alzheimer's Disease," N. Engl. J. Med. 351:56–67 (Jul. 1, 2004) at pp. 56–60.*
Bullock, Roger, "Future directions in the treatment of Alzheimer's disease," Expert Opin. Invest. Drugs 13(4): 303–314 (2004) at pp. 303, 306–309.*
Robinson, Stephen R., et al., "Lessons from the AN 1792 Alzheimer vaccine: lest we forget," Neurobiol. of Aging 25(5): 609–615 (May–Jun. 2004) at pp. 609–610.*

Lacomblez, L. et al., "Dose–ranging study of riluzole in amyotrophic lateral sclerosis," The Lancet, vol. 347(9013), pp. 1425–1431 (May 25, 1996), at p. 1429, col. 2, lines 25–26.*
Keita, H., et al., "Anesthetic concentrations of riluzole inhibit neuronal nitric oxide synthase activity, but not expression, in the rat hippocampus," Brain Research, vol. 881(2), pp. 237–240 (Oct. 2000), at p. 240, col. 1, lines 6–9 and 15–17.*
Gilgun–Sherki, Y., et al., "Riluzole suppresses experimental autoimmune encephalomyelitis; implications for the treatment of multiple sclerosis," Brain Research, vol. 989(2), pp. 196–204 (Nov. 2003), at p. 197, col. 1, lines 7–12; and p. 202, lines 27–30.*
Chabrier, P., et al., "Nitric oxide synthases: targets for therapeutic strategies in neurological diseases," Cell. Mol. Life Sci., vol. 55, pp. 1029–1035 (Sep. 1999), at p. 1029, col. 1, lines 10–18; p. 1030, col. 2, lines 7–48; p. 1032, lines 8–40, Table1.*
Lassen, L., et al., "Nitric oxide synthase inhibition in migraine," The Lancet, vol. 349, pp. 401–402 (Feb. 8, 1997), at p. 402, lines 2–5.*
Stanislaus, R., et al., "Amelioration of experimental allergic encephalomyelitis in Lewis rats by lovastatin," Neuroscience Letters, vol. 269, pp. 71–74 (Jul. 1999), at p. 73, col. 2, lines 3–8 and 31–32; and p. 74, col. 1, lines 5–15.*
Bagasra, O., et al., "Activation of the inducible form of nitric oxide synthase in the brains of patients with multiple sclerosis," Proc. Natl. Acad. Sci., vol. 92, pp. 12041–12045 (Dec. 1995), at p. 12045, col. 1, lines 1–4.*
Lee, T.J.F., "Nitric Oxide and the Cerebral Vascular Function," J. Biomed. Sci., vol. 7(1), pp. 16–26 (Jan.–Feb. 2000), at p. 23, col. 2, lines 16–17; p. 24, lines 23–35 et seq.*

(Continued)

Primary Examiner—Kamal A. Saeed
Assistant Examiner—Anthony J Paviglianiti
(74) Attorney, Agent, or Firm—Irving Newman

(57) ABSTRACT

The present invention relates to the use of 2-amino-thiazoline derivatives of formula (I):

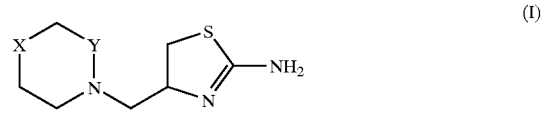

in which either Y is a methylene ($CH_2$) and X is chosen from the following groups: O, NH, (C1–C4) N-Alkyl, N—Bn, N—Ph, N-(2-Py), N-(3-Py), N-(4-Py), N-2-pyrimidyl, N-5-pyrimidyl, S, SO, $SO_2$, $CH_2$ or CHPh; or Y is a carbonyl (C=O) and X is chosen from the following groups: NH, N—Ph, N-(2-Py), N-(3-Py), N-(4-Py), N-2-pyrimidyl or N-5-pyrimidyl or pharmaceutically acceptable salts thereof as inhibitors of inducible NO-synthase.

4 Claims, No Drawings

OTHER PUBLICATIONS

Masukawa, T., et al., "Role of Nitric Oxide in the Convulsions Following the Coadministration of Enoxacin with Fenbufen in Mice," Jpn. J. Pharmacol., vol. 76(4), pp. 425–429 (Apr. 1998), at p. 428, col. 1, lines 2–12.*

Pozza, M., et al., "Further evidence for a role of nitric oxide in experimental allergic encephalomyelitis: aminoguanidine treatment modifies its clinical evolution," Brain Research, vol. 855(1), pp. 39–46 (Feb. 2000), at p. 39, col. 2, lines 5–23.*

Giovannoni, G., et al., "The potential role of nitric oxide in multiple sclerosis," Multiple Sclerosis, vol. 4(3), pp. 212–216 (Jun. 1998), at p. 213, col. 2, lines 37–62 and p. 214, col. 1, lines 8–13.*

Miljkovic, D., et al., "Leflunomide inhibits activation of inducible nitric oxide synthase in rat astrocytes," Brain Research, vol. 889(1–2), pp. 331–338 (Jan. 2001), at p. 331, col. 2, lines 5–14; p. 337, col. 2, lines 1–3.*

Torreilles, F., et al., "Neurodegenerative disorders: the role of peroxynitrite," Brain Research Reviews, vol. 30(2), pp. 153–163 (Aug. 1999), at p. 154, col. 1, lines 5–10 and 21–29; p. 158, col. 2, lines 14–40 et seq.

Milos Hudlicky, Oxidations In Organic Chemistry, American Chemical Society (1990, pp. 252–263, vol. 186).

Salvador Moncada et al., Bioynthesis Of Nitric Oxide From L–Arginine A Pathway For The Regulation Of Cell Function And Communication, Biochemical Pharmacology, (1989, pp. 1709–1715, vol. 38, No. 11).

* cited by examiner

USE OF 2-AMINO-THIAZOLINE DERIVATIVES AS INHIBITORS OF INDUCIBLE NO-SYNTHASE

This application is a Continuation of U.S. application Ser. No. 10/291,084, filed Nov. 8, 2002 now U.S. Pat. No. 6,699,867, which claimed the benefit of U.S. Provisional Application No. 60/352,797, filed Jan. 30, 2002, and which claimed the benefit of priority of French Patent Application No. 01/14,510, filed Nov. 9, 2001.

The present invention relates to the use of 2-amino-thiazoline derivatives of formula (I):

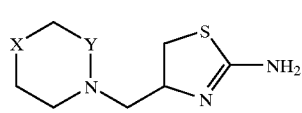

(I)

or pharmaceutically acceptable salts thereof as inhibitors of inducible NO-synthase.

The subject of the invention is the use of 2-amino-thiazoline derivatives of formula (I) and pharmaceutically acceptable salts thereof for the preparation of pharmaceutical compositions intended for preventing and treating diseases in which an abnormal production of nitric oxide (NO) by induction of inducible NO-synthase (NOS-2 ou iNOS) is involved, the pharmaceutical compositions containing the novel 2-amino-thiazoline derivatives and pharmaceutically acceptable salts thereof and the novel derivatives of 2-amino-thiazoline and pharmaceutically acceptable salts thereof.

Nitric oxide (NO) is a diffusable radical involved in many physiological and pathological processes. It is synthesized by oxidation of L-Arginine, a reaction catalyzed by a family of enzymes known as nitric oxide synthases or NO-Synthase (NOS), referenced in the international enzyme nomenclature under the number E.C. 1.14.13.39.

Three NOS isoforms, two of which are constitutive and one inducible, are known:

a neuronal NOS(NOS-1 or nNOS) was originally isolated and cloned from nerve tissue in which it is a constitutive enzyme. The NOS-1 produces NO in response to various physiological stimuli such as the activation of membrane receptors according to a mechanism dependent on calcium and on calmodulin.

an inducible NOS(NOS-2 or iNOS) can be induced in response to immunological stimuli such as, for example, cytokines or bacterial antigens in various cells such as, for example, macrophages, endothelial cells, hepatocytes, glial cells, as well as many other types of cells. This isoform activity is not regulated by calcium. Consequently, once induced, it produces a large amount of NO over prolonged periods.

an endothelial NOS (NOS-3 or eNOS) is constitutive and calcium/calmodulin dependent. It was originally identified in vascular endothelium cells, in which it generates NO in response to physiological stimuli such as the activation of membrane receptors.

The NO produced by the neuronal and endothelial constitutive isoforms (NOS-1 and NOS-3) is generally involved in intercellular signalling functions. For example, the endothelial cells which line the inner wall of blood vessels induce the relaxation of the underlying smooth muscular cells via the production de NO. It thus contributes towards regulating the arterial pressure.

The NO produced in large amount by the inducible isoform NOS-2 is, inter alia, involved in the pathological phenomena associated with acute and chronic inflammatory processes in a large variety of tissues and organs.

An excessive production of NO by induction of NOS-2 thus plays a part in degenerative pathologies of the nervous system such as, for example, multiple sclerosis, focal or global cerebral ischemia, cerebral or spinal trauma, Parkinson's disease, Huntington's disease, Alzheimer's disease, amyotrophic lateral sclerosis, migraine, depression, schizophrenia, anxiety, epilepsy. Similarly, aside the central nervous system, the induction of NOS-2 is involved in many pathologies with inflammatory components such as, for example, diabetes, atherosclerosis, myocarditis, arthritis, arthrosis, asthma, inflammatory bowel disease, Crohn's disease, peritonitis, gastroesophageal reflux, uveitis, Guillain-Barré syndrome, glomerulo-nephritis, lupus erythematosus and psoriasis. The NOS-2 was also involved in the growth of certain forms of tumors such as, for example, epitheliomas, adenocarcinomas or sarcomas, and in infections with Gram-positive or Gram-negative intracellular or extracellular bacteria.

In all the situations in which an overproduction of NO is deleterious, it thus appears to be desirable to reduce the production of NO by administering substances capable of inhibiting the NOS-2. However, given the important physiological roles played by the constitutive isoform NOS-3, in particular in regulating the arterial pressure, it is essential that the inhibition of the isoform NOS-2 has the least possible effect on the isoform NOS-3. Actually, it is known that the administration of unselective inhibitors of NOS isoforms leads to vasoconstriction and an increase in arterial pressure (Moncada, S., Palmer, R. M. J. and Higgs, E. A., Biosynthesis of nitric oxide from L-arginine: a pathway for the regulation of cell function and communication, *Biochem. Pharmacol.*, 1989, 38: 1709–1715). These effects on the cardiovascular system are deleterious since they reduce the supply of nutrients to the tissues. Consequently, the present invention relates to compounds whose inhibitory activity with respect to NOS-2 is significantly higher than their inhibitory activity with respect to NOS-3.

Thiazoline-based NOS inhibitors are described in particular in patent applications WO94/12165, WO95/11231 and WO96/14842.

The present invention relates to the use of 2-amino-thiazoline derivatives of formula (I) in which:

either Y is a methylene ($CH_2$) and X is chosen from the following groups: O, NH, N-($C_1$-$C_4$)alkyl, N—Bn, N—Ph, N-(2-Py), N-(3-Py), N-(4-Py), N-2-pyrimidyl, N-5-pyrimidyl, S, SO, $SO_2$, $CH_2$ or CHPh;

or Y is a carbonyl (C=O) and X is chosen from the following groups: NH, N—Ph, N-(2-Py), N-(3-Py), N-(4-Py), N-2-pyrimidyl, N-5-pyrimidyl for the preparation of medicinal products for preventing and treating diseases in which an abnormal production of nitric oxide (NO) by induction of inducible NO-synthase (NOS-2 or iNOS) is involved.

In the above definitions and in those which follow, the alkyl radicals contain 1 to 4 carbon atoms in a straight or branched chain. The abbreviations Bn, Py, Ph mean respectively benzyl, pyridyl, phenyl.

The compounds of formula (I) contain one or more asymmetric carbons and can thus be in racemic form or in the form of enantiomers and diastereoisomers; these also form a part of the invention as well as the mixtures thereof.

Moreover, the compounds of formula (I) can be in the tautomeric form (Ia):

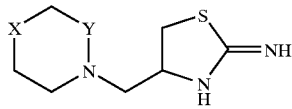

(Ia)

These tautomers also form a part of the invention.

Among the compounds of formula (I) useful according to the invention, mention may be made of the following compounds:

4-(morpholin-4-ylmethyl)-4,5-dihydro-1,3-thiazol-2-ylamine, 4-(piperazin-1-ylmethyl)-4,5-dihydro-1,3-thiazol-2-ylamine, and 4-(4-methyl-piperazin-1-ylmethyl)-4,5-dihydro-1,3-thiazol-2-ylamine, the racemic mixtures, enantiomers, diastereoisomers, tautomers thereof, as well as the pharmaceutically acceptable salts thereof.

Among the compounds useful according to the invention and particularly prefered, mention may be made of the following compound:

4-(4-methyl-piperazin-1-ylmethyl)-4,5-dihydro-1,3-thiazol-2-ylamine, the racemic mixtures, enantiomers, tautomers thereof, as well as the pharmaceutically acceptable salts thereof.

The invention also relates to the pharmaceutical compositions containing, as active principle, a derivative of formula (I) for which either Y is a methylene ($CH_2$) and X is chosen from the following groups: O, NH, N—($C_1$-$C_4$) alkyl, N—Bn, N—Ph, N-(2-Py), N-(3-Py), N-(4-Py), N-2-pyrimidyl, N-5-pyrimidyl, S, SO, $SO_2$, $CH_2$ or CHPh; or Y is a carbonyl (C=O) and X is chosen from the following groups: NH, N—Ph, N-(2-Py), N-(3-Py), N-(4-Py), N-2-pyrimidyl, N-5-pyrimidyl as well as the racemic mixtures, enantiomers, diastereoisomers, tautomer thereof, and pharmaceutically acceptable salts thereof.

The compounds of formula (I) can be prepared by cyclization of a derivative of formula (II):

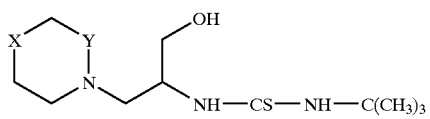

(II)

in which X and Y have the same meaning as in formula (I).

This cyclization is generally carried out using an acid such as hydrochloric acid, in aqueous medium, at a temperature of about 100° C. 6N hydrochloric acid is generally used.

The derivatives of formula (II) can be obtained according to the following reaction schemes:

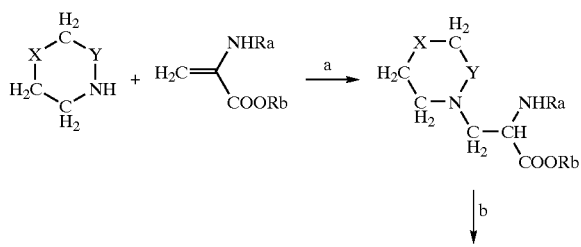

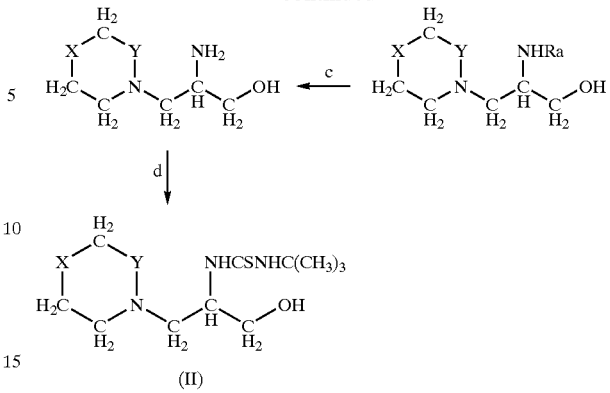

(II)

in these formulae X and Y have the same meanings as in formula (I), Ra is a protecting group of the amine function such as those described by T. W. GREENE, *Protective groups in Organic Synthesis*, J. Wiley-Interscience Publication (1991), preferably an acetyl or tert-butyloxycarbonyl radical, and Rb is a ($C_1$-$C_4$) alkyl or alkoxycarbonyl radical, preferably methyl, ethyl or isobutyloxycarbonyl.

The reaction a is generally carried out in the presence of a Lewis acid such as the iron trichloride (III), in an inert solvent such as dichloromethane or acetonitrile, at a temperature of between 10° C. and the boiling point of the reaction medium. When X represents NH, X can be protected by a protecting group of the amine function such as described by T. W. GREENE, *Protective Groups in Organic Synthesis*, J. Wiley-Interscience Publication (1991), preferably using a tert-butoxycarbonyl radical.

The reduction reaction b is preferably carried out using a hydride such as sodium borohydride or lithium aluminum hydride in a ($C_1$-$C_4$) aliphatic alcohol or tetrahydrofuran, at a temperature of between 0° C. and 30° C.

The deprotection reaction c for the compounds in which Ra is a protecting group of the amine function is carried out by any deprotection method known to those skilled in the art and in particular those described by T. W. GREENE, *Protective Groups in Organic Synthesis*, J. Wiley-Interscience Publication (1991). Preferably when the protecting group is an acetyl radical, this reaction is carried out using aqueous hydrochloric acid at a temperature of about 100° C. When the protecting group is a tert-butoxycarbonyl radical, this reaction is carried out using hydrochloric acid in dioxane, at a temperature of about 20° C.

The reaction d is carried out by the action of tert-butyl isothiocyanate, in an inert solvent such as ($C_1$-$C_4$) aliphatic alcohol (preferably methanol or ethanol), optionally in the presence of a tertiairy amine such as triethylamine, at a temperature between 20° C. and the boiling point of the reaction medium.

The compounds of formula (I) in which X represents either SO, or $SO_2$ can be obtained by direct oxidation of the compound of formula (I) in which X represents S. This oxidation is carried out according to the known methods of oxidation of organosufur compounds, such as described by M. HUDLICKY, *Oxidation in Organic Chemistry*, ACS Monograph, 186, 252–263 (1990). For example, it is carried out by the action of an organic peracid or organic peracid salt (percarboxylic or persulfonic acid, in particular perbenzoic acid, 3-chloro-perbenzoic acid, 4-nitroperbenzoic acid, peracetic acid, pertrifluoroacetic acid, performic acid, monoperphthalic acid) or a mineral peracid or mineral peracide salt (for example, periodic or persulfuric acid), in an inert solvent such as a chlorine solvent (for example, trichlorethane or dichloromethane), at a temperature of between 0° C. and 20° C. The hydrogen peroxide or periodate (sodium periodate, for example), in an inert solvent such as ($C_1$–$C_4$) aliphatic alcohol, water or a mixture of these solvents, at a temperature between 0° and 20° C. can also be used. These products can also be prepared from the corresponding compounds of formula (II), obtained according to the following reaction schemes:

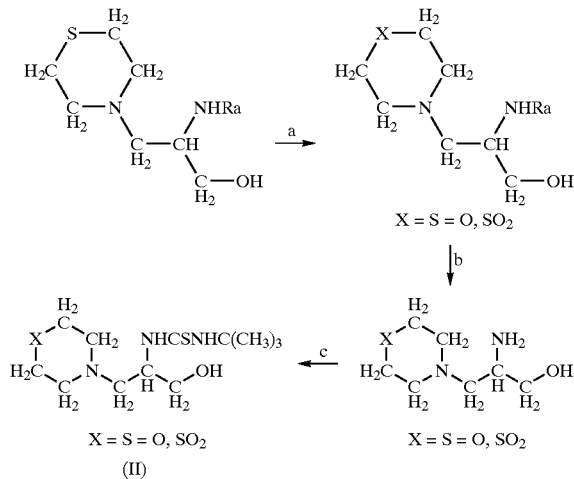

The oxidation reaction a is carried out according to the known methods of oxidation of organosulfur compounds as described above.

The deprotection reaction b for the compounds in which Ra is a protecting group of the amine function is carried out by any method of deprotection known by those skilled in the art and particularly those described by T. W. GREENE, *Protective Groups in Organic Synthesis*, J. Wiley-Interscience Publication (1991). Preferably when the protecting group is an acetyl radical, this reaction is carried out using aqueous hydrochloric acid, at a temperature of about 100° C. When the protecting group is a tert-butyloxycarbonyl radical, this reaction is carried out using an hydrochloric acid in dioxane, at a temperature of about 20° C.

The reaction c is carried out by the action of tert-butyl isothiocyanate, in an inert solvent such as ($C_1$–$C_4$) aliphatic alcohol (preferably methanol or ethanol), optionally in the presence of a tertiary amine such as triethylamine, at a temperature of between 20° C. and the boiling point of the reaction medium.

The compounds of formula (I) are isolated and can be purified by the usual known methods, for example crystallization, chromatography or extraction.

The enantiomers of the compounds of formula (I) can be obtained by resolving the racemic mixtures, for example by chromatography on a chiral column according to PIRCKLE W. H. et al., *Asymmetric Synthesis, Vol.* 1, Academic Press (1983) or by formation of salts or by synthesis from chiral precursors. The diastereoisomers can be prepared according to the known conventional methods (crystallization, chromatography or from chiral precursors).

The compounds of formula (I) can optionally be converted to addition salts with a mineral or organic acid by the the action of such an acid in an organic solvent such as an alcohol, a ketone, an ether or a chlorinated solvent. These salts also form a part of the invention.

Examples of pharmaceutically acceptable salts which may be mentioned are the following salts: benzenesulfonate, hydrobromide, hydrochloride, citrate, ethanesulfonate, fumarate, gluconate, iodate, isethionate, maleate, methanesulfonate, methylenebis-β-oxynaphtoate, nitrate, oxalate, pamoate, phosphate, salicylate, succinate, sulfate, tartrate, theophyllinacetate and p-toluenesulfonate.

The compounds of formula (I) are inhibitors of NO-synthase inducible or NO-synthase of type 2 (NOS-2) and are thus useful for preventing and treating disorders associated with an excessive NO production such as mutiple sclerosis, focal or global cerebral ischemia, cerebral or spinal trauma, Parkinson's disease, Huntington's disease, Alzheimer's disease, amyotrophic lateral sclerosis, migraine, depression, schizophrenia, anxiety, epilepsy, diabetes, atherosclerosis, myocarditis, arthritis, arthrosis, asthma, inflammatory bowel disease, Crohn's disease, peritonitis, gastro-esophageal reflux, uveitis, Guillain-Barré syndrome, glomerulo-nephritis, lupus erythematosus and psoriasis, the growth of certain forms of tumors such as for example epitheliomas, adenocarcinomas or sarcomas, and in infections with Gram-positive or Gram-negative intracellular or extracellular bacteria.

Their activities as inhibitors of NOS-2 and NOS-3 were determined by measuring the conversion of [$^3$H]-L-arginine into [$^3$H]-L-citrulline with, respectively, a NOS-2 enzymatic fraction extracted from the lungs of rats or mices pretreated with lipopolysaccharides (10 mg/kg i.p. 6 hours before collecting the tissue) and with a commercial preparation of recombinant bovine NOS-3. The compounds were incubated for 20 to 30 minutes at 37° C. in the presence of 5 $\mu$M (for NOS-2 activity) or 10 $\mu$M (for NOS-3 activity) of [$^3$H]-L-arginine, 1 mM of NADPH, 15 $\mu$M of tetrabiopterine, 1 $\mu$M of FAD, 0.1 mM of DTT in a HEPES buffer (50 mM, pH 6.7) containing 10 $\mu$g/ml of calmodulin and 1.25 mM of $CaCl_2$ when the NOS-3 activity was measured. The incubation was stopped by adding cold HEPES buffer (100 mM, pH 5.5) containing 10 mM EGTA and 500 mg of cationic ion-exchange resin (AG50W-X8, counter-ion: $Na^+$) to separate the [$^3$H]-L-arginine from the [$^3$H]-L-citrulline. After separation of the phases by settling for 5 min, the radioactivity remaining in the liquid phase was measured in a scintillation counter in the presence of a suitable scintillation liquid. The yield for the recovery of the formed L-[$^3$H]citrulline was able to be estimated using L-[ureido-$^{14}$C]-citrulline as external standard.

The NOS-2 or NOS-3 activity was expressed in picomole(s) of [$^3$H]-L-citrulline formed per minute and per milligram of protein contained in the rection medium.

In this test on the enzyme NOS-2, the $IC_{50}$ value for the compounds of formula (I) is less than or equal to 10 $\mu$M.

The selectivity is measured by the $IC_{50}$ NOS-3/$IC_{50}$ NOS-2 ratio. This selectivity is greater than 45.

The compounds of formula (I) are of low toxicity. Their $LD_{50}$ is greater than 40 mg/kg via cutaneous route in mice.

The following examples illustrate the invention.

EXAMPLE 1

4-(4-Methyl-piperazin-1-ylmethyl)-4,5-dihydro-thiazol-2-ylamine trihydrochloride

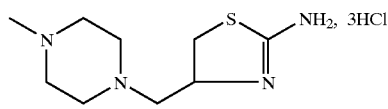

A suspension of 0.42 g de N-(tert-butyl)-N'-[2-hydroxy-1-(4-methyl-piperazin-1-ylmethyl)ethyl]-thiourea in 3.9 mL of an aqueous 6N hydrochloric acid is heated at a temperature of about 100° C. for 5 hours. After cooling, the reaction medium is concentrated under reduced pressure (2 kPa) at a temperature of about 55° C. The residue obtained is dried in an oven under vacuum (2 kPa) for 4 hours. About 0.47 g of 4-(4-methyl-piperazin-1-ylmethyl)-4,5-dihydro-thiazol-2-ylamine, trihydrochloride are obtained in the form of a very hygroscopic off-white paste. [$^1$H NMR spectrum (300 MHz, (CD$_3$)$_2$SO d6 with addition of a few drops of CD$_3$COOD d4. δ in ppm): from 2.55 to 2.90 (mf, 4H); 2.80 (s, 3H); from 2.95 to 3.30 (mf, 4H); from 3.30 to 3.60 (mf, 2H); 3.40 (dd, J=11.5 and 5.5 Hz, 1H); 3.69 (dd, J=11.5 and 7.5 Hz, 1H); 4.51 (mt, 1H)].

N-(tert-Butyl)-N'-[2-hydroxy-1-(4-methyl-piperazin-1-ylmethyl)ethyl]-thiourea

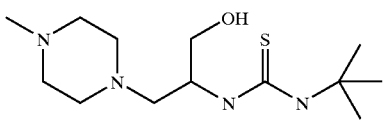

To a solution of 1 g of 2-amino-3-(4-methyl-piperazin1-yl)-1-propanol hydrochloride in 20 mL of absolute ethanol and 1.43 mL of triethylamine, about 0.78 mL of tert-butylisothiocyanate are added. The reaction mixture is stirred under inert atmosphere at a temperature of about 20° C. for 42 hours then is heated at a temperature of about 50° C. for 1 hour 30 min. After cooling at a temperature of about 20° C., the reaction medium is evaporated under reduced pressure (2 kPa) at a temperature of about 30° C. The residue thus obtained is taken up in 10 mL of water and 40 mL of dichloromethane. The aqueous phase is extracted with 2 times 30 mL of dichloromethane. The organic phases are collected, washed with 15 mL of water, dried over magnesium sulfate, filtered, then concentrated under reduced pressure (2 kPa) at a temperature of about 20° C. About 0.42 g of N-(tert-butyl)-N'-[2-hydroxy-1-(4-methyl-piperazin-1-ylmethyl)ethyl]thiourea are obtained in the form of a white paste. [Infrared spectrum between lamella of KBr 3279; 3075; 2939; 2806; 1533; 1459; 1359; 1295; 1204; 1010 and 821 cm$^{-1}$].

2-Amino-3-(4-methyl-piperazin-1-yl)-1-propanol hydrochloride

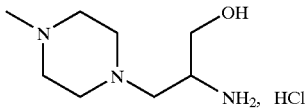

A suspension of 0.89 g of N-[2-hydroxy-1-(4-methyl-piperazin-1-ylmethyl)ethyl] acetamide in 10.3 mL of an aqueous acid solution of 6N hydrochloric acid is heated at a temperature of about 100° C. for 3 hours. After cooling at a temperature of about 60° C., the reaction medium is filtered and the filtrate is concentrated under reduced pressure (2 kPa) at a temperature of about 60° C. About 1 g of 2-amino-3-(4-methyl-piperazinyl)-1-propanol, hydrochloride is obtained in the form of a tacky beige-colored paste. [Infrared spectrum (KBr) 3337; 2955; 2637; 2522; 1617; 1457; 1062; 1009 and 962 cm$^{-1}$].

N-[2-Hydroxy-1-(4-methyl-piperazin-1-ylmethyl)ethyl]acetamide

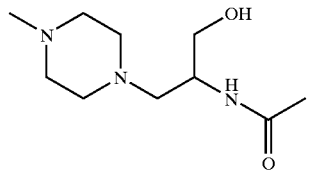

A solution under inert atmosphere of 3.27 g of methyl (acetylamino)-3-(4-methyl-piperazin-1-yl)propanoate in 100 mL of anhydrous methanol is cooled at a temperature of about 10° C., then 0.76 g of sodium borohydride are added using a spatula. The reaction medium is stirred for 5 hours at a temperature of about 20° C., then are added again 0.26 g of sodium borohydride and the stirring is carried out for 38 hours. Then, 5 mL of water is dropped into the reaction mass which is heated and concentrated under reduced pressure (2 kPa) at a temperature of about 30° C. The obtained residue is taken up with dichloromethane and the insoluble matter is removed by filtration. The filtrate is concentrated under reduced pressure (2 kPa) at a temperature of about 20° C. The residue is purified by chromatography under argon pressure (60 kPa), on a column of silica gel (particle size 40–63 μm; diameter 5 cm; height 19 cm), eluting with successive mixtures of 20% dichloromethane/methanol/aqueous ammonia (98/2/0, 95/5/0.1, 90/10/0.2, 80/20/0.25, 50/50/0.25 by volume). The fractions containing the expected product are combined and concentrated under reduced pressure (2 kPa) at a temperature of about 40° C. About 0.92 g of N-[2-hydroxy-1-(4-methyl-piperazin-1-ylmethyl)ethyl] acetamide are obtained in the form of a yellow-colored liquid. [Infrared spectrum CH$_2$Cl$_2$ 3621; 3429; 3352; 2944; 2803; 1657; 1513; 1460; 1284; 1050; 1011 and 816 cm$^{-1}$].

2-(Acetylamino)-3-(4-methyl-piperazin-1-yl) propanoate de methyle

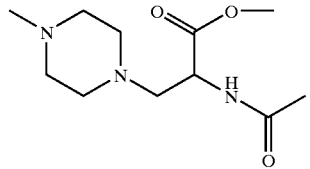

To a solution of 8.57 g of methyl 2-acetamidoacrylate in 500 mL of dichloromethane stirred under inert atmosphere, about 6.65 mL of N-methylpiperazine are added, then 0.97 g of iron trichloride are added, and the mixture is stirred at a temperature of about 20° C. for 66 hours. Then, 300 mL of an aqueous solution of sodium sulfate are dropped to the reaction medium while stirring the reaction mixture and the mixture filtered through Celite. After separation of the phase by settling, the organic phase is dried over sodium sulfate, filtered and then concentrated in a vacuum oven under reduced pressure (2 kPa) at a temperature of about 40° C. in order to obtain an orange-colored liquid. The aqueous phase is extracted with 3 times 150 mL of dichloromethane and all of the organic extracts are collected, dried over sodium sulfate, then concentrated under reduced pressure (2 kPa) at a temperature of about 20° C. in order to obtain an yellow oil. Both of the organic extracts as described above are combined and purified by chromatography under argon pressure (50 kPa), on a column of silica gel (particle size 40–63 µm; diameter 5 cm; height 25 cm), eluting with successive mixtures of 20% dichloromethane/methanol/aqueous ammonia (99/1/0, 97/3/0, 90/10/0.25, 80/20/0.25 by volume). The fractions containing the expected product are combined and concentrated under reduced pressure (2 kPa) at a temperature of about 30° C. About 3.3 g of methyl 2-(acetylamino)-3-(4-methyl-piperazinyl)propanoate are obtained in the form of a yellow liquid. [Infrared spectrum $CCl_4$ 3437; 3318; 2941; 2798; 1749; 1685; 1499; 1458; 1374; 1286; 1204; 1168 and 1014 $cm^{-1}$ ]

The pharmaceutical compositions according to the invention consist of a compound of formula (I) or an isomer or tautomer or salt of such a compound, in pure form or in the form of a composition in which it is combined with any other pharmaceutically compatible product, which may be inert or physiologically active. The medicinal products according to the invention may be used orally, parenterally, rectally or topically.

Solid compositions for oral administration which can be used include tablets, pills, powders (gelatin capsules, cachets) or granules. In these compositions, the active principle according to the invention is mixed with one or more inert diluents, such as starch, cellulose, sucrose, lactose or silica, under a stream of argon. These compositions can also comprise substances other than diluents, for example, one or more lubricants such as magnesium stearate or talc, a dye, a coating (dragées) or a varnish.

Liquid compositions for oral administration which can be used include pharmaceutically acceptables solutions, suspensions, emulsions, syrups and elixirs containing inert diluents such as water, ethanol, glycerol, plant oils or liquid paraffin. These compositions can comprise substances other than diluents, for example, wetting products, sweeteners, thickeners, flavorings or stabilizers.

The sterile compositions for parenteral administration can preferably be aqueous or non-aqueous solutions, suspensions or emulsions. Solvent or vehicles which may be used include water, propylene glycol, a polyethylene glycol, plant oils, in particular, olive oil, injectable organic esters, for example ethyl oleate, or other suitable organic solvents. These compositions can also contain adjuvants, in particular, wetting agents, solvents. These compositions can also contain adjuvants, in particular, wetting agents, isotonic agents, emulsifiers, dispersants and stabilizers. The sterilization can be carried out in several ways, for example, by aseptic filtration, by incorporating sterilizing agents into the composition, by irradiation or by heating. They can also be prepared in the form of sterile solid compositions which can be dissolved at the time of use in sterile water or any other injectable sterile medium The compositions for rectal administration are suppositories or rectal capsules which contain, besides the active product, excipients such as cocoa butter, semi-synthetic glycerides or polyethylene glycols.

The compositions for topical administration can be, for example, creams, lotions, eye drops, mouth washes, nasal drops or aerosols.

In human therapy, the compounds according to the invention are particularly useful for treating and/or preventing multiple sclerosis, focal or global cerebral ischemia, cerebral or spinal trauma, Parkinson's disease, Huntington's disease, Alzheimer's disease, amyotrophic lateral sclerosis, migraine, depression, schizophrenia, anxiety, epilepsy, diabetes, atherosclerosis, myocarditis, arthritis, arthrosis, asthma, inflammatory bowel disease, Crohn's disease, peritonitis, gastro-esophageal reflux, uveitis, Guillain-Barré syndrome, glomerulo-nephritis, lupus erythematosus, psoriasis, the growth of certain forms of tumors such as, for example, epitheliomas, adenocarcinomas or sarcomas, and in infections with Gram-positive or Gram-negative intracellular or extracellular bacteria.

The doses depend on the disired effect, the duration of the treatment and the route of administration used; they are generally comprised between 1 mg and 100 mg per day via the oral route for an adult, with unit doses ranging from 0.5 mg to 50 mg of active substance.

The examples which follow illustrate compositions according to the invention:

EXAMPLE A

Gel capsules containing 50 mg of active product and having the composition below are prepared, according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing 50 mg of active product and having the composition below are prepared, according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerol, titanium oxide (72/3.5/24.5) q.s. 1 finished film-coated tablet weighing | 245 mg. |

EXAMPLE C

An injectible solution containing 10 mg of active product having the following composition:

| | |
|---|---|
| Compound of formula (I) | 10 mg |
| Benzoic acid | 80 mg |
| Benzyl alcohol | 0.06 ml |
| Sodium benzoate | 80 mg |
| 95% ethanol | 0.4 ml |
| Sodium hydroxide | 24 mg |
| Propylene glycol | 1.6 ml |
| Water q.s | 4 ml |

The present invention also relates to the method for preventing and treating diseases in which an abnormal production of nitric oxide (NO) by induction of inducible NO-synthase (NOS-2 or iNOS) is involved by administration of a compound of formula (I), the racemic mixtures, enantiomers, diastereoisomers thereof and mixtures thereof, tautomer thereof and pharmaceutically acceptable salts thereof.

We claim:

1. A method of inhibiting excess nitric oxide (NO) production in a mammal in need thereof to treat an illness selected from the group consisting of multiple sclerosis, cerebral, focal or global ischemia, cerebral or spinal trauma, Parkinson's disease, Huntington's disease, Alzheirner's disease, amyotrophic lateral sclerosis, migraine, depression, schizophrenia, anxiety and epilepsy, said method comprising administering to said mammal an effective inducible nitric oxide synthase (i-NOS) inhibiting amount of a compound of formula (I):

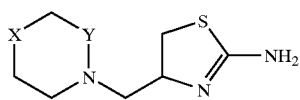

(I)

wherein either Y is (CH$_2$) and X is chosen from the following group: O, NH, N—(C$_1$–C$_4$)alkyl, N-benzyl, N-phenyl, N-(2-pyridyl), N-(3-pyridyl), N-(4-pyridyl), N-2-pyrimidyl, N-5-pyrimidyl, S, SO, SO$_2$, CH$_2$ and CHPh;

or Y is (C═O) and X is chosen from the following group: NH, N-phenyl, N-(2-pyridyl), N-(3-pyridyl), N-(4-pyridyl), N-2-pyrimidyl and N-5-pyrimidyl;

wherein the (C$_1$–C$_4$)alkyl contains 1 to 4 carbon atoms in a straight or branched chain; or a racemic mixture, an enantiomer, a diastereoisomer or a mixture thereof, or a tautomer thereof, or a pharmaceutically acceptable salt thereof, optionally in combination with a pharmaceutically acceptable carrier.

2. The method according to claim 1, wherein the compound of formula (I) is chosen from the following compounds:

4-(morpholin-4-ylmethyl)-4,5-dihydro-1,3-thiazol-2-ylamine, 4-(piperazin-1-ylmethyl)-4,5-dihydro-1,3-thiazol-2-ylamine, and 4-(4-methyl-piperazin-1-ylmethyl)-4,5-dihydro-1,3-thiazol-2-ylamine, or a racemic mixture, an enantiozner, a diastereoisomer or a mixture thereof, or a tautomer thereof, or a pharmaceutically acceptable salt thereof.

3. The method according to claim 1, wherein the compound of formula (I) is 4-(4-methyl-piperazin-1-ylmethyl)-4,5-dihydro-1,3-thiazol-2-ylamine or a racemic mixture, an enantiomer, or a tautomer thereof, or a pharmaceutically acceptable salt thereof.

4. The method according to claim 1, wherein the illness is Parkinson's disease.

* * * * *